US009510570B2

(12) United States Patent
Tang et al.

(10) Patent No.: US 9,510,570 B2
(45) Date of Patent: Dec. 6, 2016

(54) CD81 AND OCLN DOUBLE TRANSGENIC MOUSE AND ITS CONSTRUCTION METHODS

(71) Applicant: WUHAN INSTITUTE OF VIROLOGY, CAS, Wu Han (CN)

(72) Inventors: Hong Tang, Wu Han (CN); Xin-Wen Chen, Wu Han (CN); Ji-Zheng Chen, Wu Han (CN); Yang Zhao, Wu Han (CN); Chao Zhang, Wu Han (CN); Hai-Rong Chen, Wu Han (CN)

(73) Assignee: Wuhan Institute of Virology, CAS, Wuhan (CN)

( * ) Notice: Subject to any disclaimer, the term of this patent is extended or adjusted under 35 U.S.C. 154(b) by 0 days.

(21) Appl. No.: 14/313,109

(22) Filed: Jun. 24, 2014

(65) Prior Publication Data

US 2015/0113673 A1    Apr. 23, 2015

(30) Foreign Application Priority Data

Oct. 23, 2013  (CN) .......................... 2013 1 0502450

(51) Int. Cl.
| | | |
|---|---|---|
| *G01N 33/00* | (2006.01) | |
| *A01K 67/027* | (2006.01) | |
| *A01K 67/033* | (2006.01) | |
| *A01K 67/02* | (2006.01) | |

(52) U.S. Cl.
CPC ........... *A01K 67/0275* (2013.01); *A01K 67/02* (2013.01); *A01K 67/0278* (2013.01); *A01K 2217/052* (2013.01); *A01K 2227/105* (2013.01); *A01K 2267/0337* (2013.01)

(58) Field of Classification Search
USPC ........................................... 800/3, 18, 9, 25
See application file for complete search history.

(56) References Cited

U.S. PATENT DOCUMENTS

| | | | | |
|---|---|---|---|---|
| 4,873,191 | A * | 10/1989 | Wagner ..................... | A01H 1/00 435/317.1 |
| 5,354,674 | A * | 10/1994 | Hodgson ................ | C12N 15/63 435/235.1 |
| 6,414,220 | B1 * | 7/2002 | Vrontakis ............ | C07K 14/575 435/320.1 |
| 2005/0149998 | A1 * | 7/2005 | Capecchi ............... | C07K 14/47 800/14 |
| 2011/0271356 | A1 * | 11/2011 | Ploss et al. ........................ | 800/9 |
| 2012/0107284 | A1 * | 5/2012 | Kozlova .............. | C12N 5/0623 424/93.21 |

OTHER PUBLICATIONS

Tong et al., Tupaia CD81, Sr—Bi, Claudin-1, and Occludin Support Hepatitis C Virus Infection Journal of Virology, Mar. 2011, p. 2793-2802.*
Capecchi et al., 2005 Gene targeting in mice: functional analysis of the mammalian genome for the twenty-first century Nature Reviews | Genetics pp. 507-512.*
Gama Sosa et al., Animal transgenesis: an overview Brain Struct Funct (2010) 214:91-109.*
pLIVE In Vivo Expression and Reporter Vectors, downloaded on 4/12/201.*
Aloisi, F., and R. Pujol-Borrell. 2006. Lymphoid neogenesis in chronic inflammatory diseases. Nat Rev Immunol 6:205-217.
Bukh, J. 2004. A critical role for the chimpanzee model in the study of hepatitis C. Hepatology 39:1469-1475.
Carithers, R.L., Jr., D. Sugano, and M. Bayliss. 1996. Health assessment for chronic HCV infection: results of quality of life. Dig Dis Sci 41:75S-80S.
Chisari, F.V. 2005. Unscrambling hepatitis C virus-host interactions. Nature 436:930-932.
Dorner, M., J.A. Horwitz, B.M. Donovan, R.N. Labitt, W.C. Budell, T. Friling, A. Vogt, M.T. Catanese, T. Satoh, T. Kawai, S. Akira, M. Law, C.M. Rice, and A. Ploss. 2013. Completion of the entire hepatitis C virus life cycle in genetically humanized mice. Nature 501:237-241.
Dorner, M., J.A. Horwitz, J.B. Robbins, W.T. Barry, Q. Feng, K. Mu, C.T. Jones, J.W. Schoggins, M.T. Catanese, D.R. Burton, M. Law, C.M. Rice, and A. Ploss. 2011. A genetically humanized mouse model for hepatitis C virus infection. Nature 474:208-211.
Han, Q., C. Xu, C. Wu, W. Zhu, R. Yang, and X. Chen. 2009. Compensatory mutations in NS3 and NS5A proteins enhance the virus production capability of hepatitis C reporter virus. Virus Res 145:63-73.
Kaul, A., I. Woerz, P. Meuleman, G. Leroux-Roels, and R. Bartenschlager. 2007. Cell culture adaptation of hepatitis C virus and in vivo viability of an adapted variant. J Virol 81:13168-13179.
Maheshwari, A., S. Ray, and P.J. Thuluvath. 2008. Acute hepatitis C. Lancet 372:321-332.
Moriya, K., H. Fujie, Y. Shintani, H. Yotsuyanagi, T. Tsutsumi, K. Ishibashi, Y. Matsuura, S. Kimura, T. Miyamura, and K. Koike. 1998. The core protein of hepatitis C virus induces hepatocellular carcinoma in transgenic mice. Nat Med 4:1065-1067.
Tong, Y., Y. Zhu, X. Xia, Y. Liu, Y. Feng, X. Hua, Z. Chen, H. Ding, L. Gao, Y. Wang, M.A. Feitelson, P. Zhao, and Z.T. Qi. 2011. Tupaia CD81, Sr—Bi, claudin-1, and occludin support hepatitis C virus infection. J Virol 85:2793-2802.
Washburn, M.L., M.T. Bility, L. Zhang, G.I. Kovalev, A. Buntzman, J.A. Frelinger, W. Barry, A. Ploss, C.M. Rice, and L. Su. 2011. A humanized mouse model to study hepatitis C virus infection, immune response, and liver disease. Gastroenterology 140:1334-1344.
Xinping Xu, Hongbo Chen, Xiaomei Cao and Kunlong Ben, 2007, Efficient infection of tree shrew (Tupaia belangeri) with hepatitis C virus grown in cell culture or from patient plasma, J General Virology, 88, 2504-2512.

* cited by examiner

*Primary Examiner* — Maria Leavitt
(74) *Attorney, Agent, or Firm* — Wang Law Firm, Inc.

(57) ABSTRACT

The present invention provides a CD81 and OCLN double transgenic mouse and its construction method and use. The double transgenic mouse can be used to constitute acute and chronic HCV infection in a mouse model.

9 Claims, 13 Drawing Sheets

CD81 AND *OCLN* DOUBLE TRANSGENIC MOUSE AND ITS CONSTRUCTION METHODS

BACKGROUND OF THE INVENTION

1. Field of the Invention

The present invention relates generally to a field of transgenic technology, and more particularly relates to a CD81 and OCLN double transgenic mouse and its construction methods and uses.

2. Description of the Prior Arts

Hepatitis C is widespread in the world, as currently there are about 1.3-1.7 million hepatitis C patients. Nearly 80% HCV infected population develops chronic infections, and some of chronic hepatitis C will progress to liver fibrosis, cirrhosis and liver cancer. The HCV is divided into different hypotypes among different races, and the clinic treatments for various HCV hypotypes are also accordingly different. While no vaccine is currently available, effective prevention and treatment for hepatitis C have become a major health issue in need of solution.

The basic studies of HCV infectious and pathogenic mechanism as well as the development of drugs and vaccines would likely benefit from suitable animal models. Chimpanzees are the only species besides humans that is susceptible to HCV infection. However, small number, high costs, slow reproduction, primate animal welfare and growing ethical concerns will limit access to the chimpanzee model, and thus development of suitable alternatives is critical. So far, the development of small animal model of HCV has made some progress, including:

(1) Full-length transgenic mouse: HCV mouse model is developed by transgening HCV full-length genome or specific protein fragment to mouse genome to construct a transgenic mouse having persistent HCV protein expression (Moriya et al., 1998, *The core protein of hepatitis C virus induces hepatocellular carcinoma in transgenic mice*, Nat Med 4:1065-1067.). The HCV gene overexpression in the transgenic mouse somatic cell would cause expression pressure on the host cell. Such mouse model only expresses HCV gene fragment and lacks the process of HCV virus particles invasion and replication in the cells, such that its application is very limited.

(2) The tree shrew model: tree shrews are susceptible to HCV infection (Tong et al., 2011 *Tupaia CD81, SR-BI, claudin-1, and occludin support hepatitis C virus infectio*, J Virol 85:2793-2802; Xu et al., 2007). However, said infection is a transient infection, and this model is unable to establish a stable and reproducible infection. As the tree shrew is a wild animal, artificial feeding and breeding cannot be easily sustained, and its genetic strains are unstable, making it unsuitable for long-term research and application.

(3) Chimeric mouse model: engrafting primary human liver cells to immunodeficient mice or embedding human liver tissue into renal capsular of the mice can support HCV infection and replication. However, this model is limited by low efficiency of viral infection, human liver tissue or cellular immune rejection, and lack of immune response against the pathology of HCV. For example, urokinase-type plasminogen-activator gene (uPA) expression is regulated by albumin promoter (specifically expressed in liver) in severe combined immunodeficiency (SCID) mice would cause persistent liver damage (Kaul et al., 2007, *Cell culture adaptation of hepatitis C virus and in vivo viability of an adapted variant*. J Virol 81:13168-13179).

(4) SCID mice transplanted with human liver cell and immune system has limited HCV expression with partial hepatitis pathological process. Moreover, the technology is complex, SCID mice are not readily available, HCV infection is also unstable, and ethical concerns are involved. For example, FK506 binding protein and caspase 8 fusion protein are regulated by albumin promoter in the immunodeficient Balb/C mice having Rag2$^{-/-}$IL2rg$^{-/-}$, such that the mice can induce liver damage and then accept human liver cell transplantation after induction (Washburn et al., 2011, *A humanized mouse model to study hepatitis C virus infection, immune response, and liver disease*, Gastroenterology 140: 1334-1344.).

(5) Studies have shown that the species specification of HCV infection depends on the infected subject. The mouse transplanted with CD81 of HCV cell receptor and OCLN (Occludin) can support virus infection and replication in the cellular level. HCV replication in mouse hepatocytes can be detected by adenovirus vector carrying CD81 and OCLN in mouse hepatocytes after transient expression, but cannot establish infection and hepatitis pathological variation. For example, the four HCV receptor genes carried by adenoviral vector can express in mouse, and induce HCV to be able to enter mouse cell for replication. However, the life-cycle of HCV in this model is not complete and hepatitis pathological processes cannot be duly observed (Dorner et al., 2011, *A genetically humanized mouse model for hepatitis C virus infection*. Nature 474:208-211.).

SUMMARY OF THE INVENTION

The present invention firstly provides a CD81 and OCLN double transgenic mouse model, wherein the mouse model is constructed by the following steps:

(1) inserting human CD81 and OCLN clonings to a pLIVE® vector respectively to obtain a pLIVE-CD81 vector containing CD81 gene expression and a pLIVE-OCLN vector containing OCLN gene expression;

(2) construction a CD81 and OCLN double transgenic mouse:

restricting the pLIVE-CD81 vector and the pLIVE-OCLN vector respectively to obtain linear DNA fragments comprising CD81 and linear DNA fragments comprising OCLN respectively;

microinjecting the linear DNA fragments comprising CD81 and the linear DNA fragments comprising OCLN respectively into ICR mice zygotes respectively;

transplanting the ICR mice zygotes to pseudopregnant ICR mice uteruses to breed CD81 transgenic mice and OCLN transgenic mice respectively, and then confirmed by PCR identification; and backcrossing the CD81 transgenic mice and the OCLN transgenic mice to obtain the CD81 and OCLN double transgenic mice.

The present invention also provides a CD81 and OCLN double transgenic mouse whose genome contains transgenes comprising nucleic acids encoding CD81 and OCLN respectively, thereby promoting HCV natural infection and pathologic process of hepatitis C so that expressions of CD81 and OCLN are persistent.

The present invention also provides a method for constructing a CD81 and OCLN double transgenic mice model, wherein the method is constituted by the following steps:

(1) inserting human CD81 and OCLN clonings into a pLIVE® vector to obtain a pLIVE-CD81 vector containing CD81 gene expression and a pLIVE-OCLN vector containing OCLN gene expression;

(2) constructing CD81 and OCLN double transgenic mice:

restricting the pLIVE-CD81 vector and the pLIVE-OCLN vector respectively to obtain linear DNA fragments comprising CD81 and linear DNA fragments comprising OCLN respectively;

microinjecting the linear DNA fragments comprising CD81 and the DNA fragments comprising OCLN into ICR mice zygotes respectively;

transplanting the ICR mice zygotes to pseudopregnant ICR mice uteruses to breed CD81 transgenic mice and OCLN transgenic mice respectively, and then confirmed by PCR identification; and backcrossing the CD81 transgenic mice and the OCLN transgenic mice to obtain the CD81 and OCLN double transgenic mice ($C/O^{Tg}$).

In brief, the method for constructing the CD81 and OCLN double transgenic mice ($C/O^{Tg}$) model comprising the following specific steps:

(1) human CD81 and OCLN gene clonings:

amplifying human CD81 and OCLN cDNA fragments by PCR from human cDNA library to obtain CD81 and OCLN encoding DNAs (cDNA) respectively, wherein the DNA sequences are SEQ ID NO. 1 and SEQ ID NO. 2;

inserting CD81 cDNA into the pLIVE® vector in restriction sites between XhoI and BamHI endonuclease to obtain a pLIVE-CD81 vector containing CD81 expression;

inserting OCLN DNA (cDNA) into the pLIVE® vector in restriction sites between SalI and XhoI endonuclease to obtain a pLIVE-OCLN vector containing OCLN expression;

wherein the pLIVE® vector comprises mouse α-fetoprotein (AFP) enhancer and mouse albumin promoter for expressing in liver efficiently, specifically, stably and extendedly;

(2) construction of CD81 and OCLN double transgenic mice:

excising the pLIVE-CD81 vector by BglII and NdeI endonuclease to obtain linear CD81 DNA fragments (represented by SEQ ID NO. 3); excising the pLIVE-OCLN vector by SalI and XhoI endonuclease to obtain linear OCLN DNA fragments (represented by SEQ ID NO. 4);

diluting each DNA fragment to 1 ng/mL and microinjecting the diluted DNA fragments into ICR mice zygotes respectively;

transplanting the ICR mice zygotes to pseudopregnant ICR mice uterus to breed CD81 transgenic mice ($CD81^{Tg/-}$) and OCLN transgenic mice ($OCLN^{Tg/-}$) respectively, and then confirmed by PCR identification; and, backcrossing the CD81 transgenic mice and the OCLN transgenic mice to obtain the CD81 and OCLN double transgenic mice ($CD81^{Tg/-}OCLN^{Tg/-}$, abbreviating $C/O^{Tg}$).

The CD81 and OCLN double transgenic mice model of the present invention described that two human CD81 and OCLN genes of the HCV receptor can be integrated stably and expressed in mouse gonome by integrating CD81 and OCLN genes into mouse chromosome respectively for breeding the CD81 and OCLN double transgenic mice, but two transgenes do not affect host allelic gene. The impaction is small for the host and can be used to support HCV entry.

The present invention also provides a method for constituting acute and chronic HCV infection model of the CD81 and OCLN double transgenic mice. Because the HCV replication is susceptible to antiviral drugs such as nucleotide analogues or protease inhibitors, the described model can validate the efficacy against HCV antiviral drug, antiviral evaluation of immunomodulatory agents, optimization of clinical treatment, and vaccine development.

HCV natural infection and pathological process can be reproduced in mice having complete immune system because of permanent HCV replication and HCV viral load of liver and stable peripheral blood, so as to establish acute and chronic infection and liver pathology models.

The CD81 and OCLN double transgenic mice of the present invention is first constructed. The method for constructing this transgenic mice model is stable and can be reproduced in bulk.

The CD81 and OCLN double transgenic mice of the present invention can provide a persistent infection model that completely reflects HCV natural infection and pathologic process of hepatitis C.

Furthermore, the CD81 and OCLN double transgenic mice of the present invention can also be used to develop various diagnosis, detection techniques, methods and products against HCV.

The present invention also provides bioactive substances from the CD81 and OCLN double transgenic mice during HCV infection via blood, wherein the bioactive substances include, but not limited to, antibodies, neutralizing, antigen presenting cells and HCV specific T cells.

The CD81 and OCLN double transgenic mice of the present invention also provides a variety of HCV mutants that can be used for drug design and vaccine development.

DETAILED DESCRIPTION OF THE PREFERRED EMBODIMENTS

Other objectives, advantages and novel features of the invention will become more apparent from the following detailed description when taken in conjunction with the accompanying drawings.

ICR mice: CD-1® mice were purchased from Vital River Laboratory Animal Technology Co. Ltd.

pLIVE® vector was purchased from Minis Corporation. The pLIVE® vectors are covered by patents pending of Minis Bio LLC. The pLIVE® vectors are sustained long-term gene expression in the liver post hydrodynamic tail vein injection, and available with positive control vectors expressing either LacZ or human placental secreted alkaline phosphatase (SEAP).

Example 1

Construction of CD81 and OCLN Double Transgenic Mice

Figure 1A:
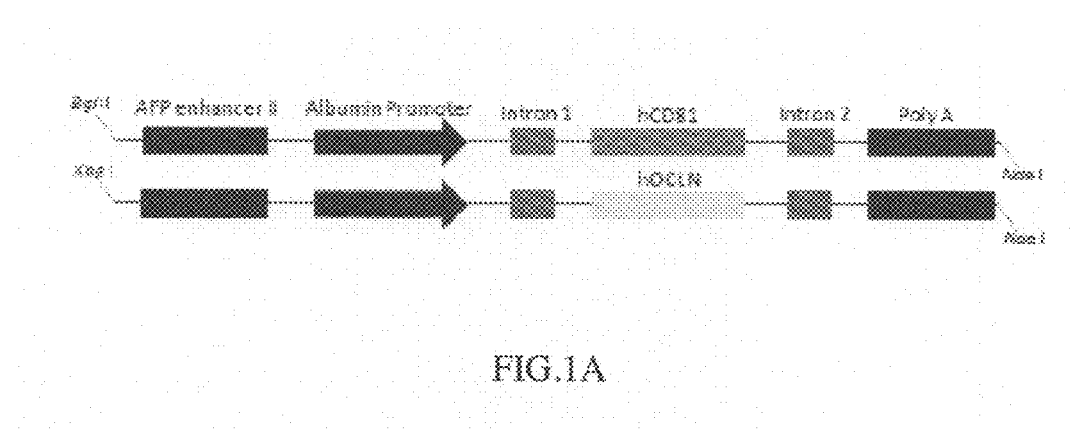
FIG. 1A provides transgenic plasmid maps comprising human CD81 and OCLN genes respectively.
Figure 1B:
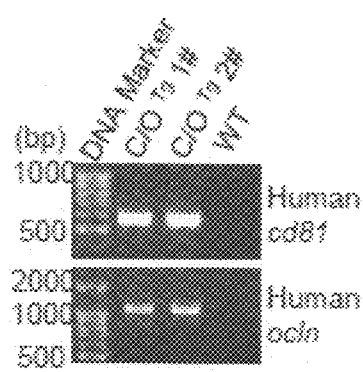
FIG. 1B illustrates the genotype of the double transgenic mice obtained from tail by DNA extraction and PCR.
Figure 1C:
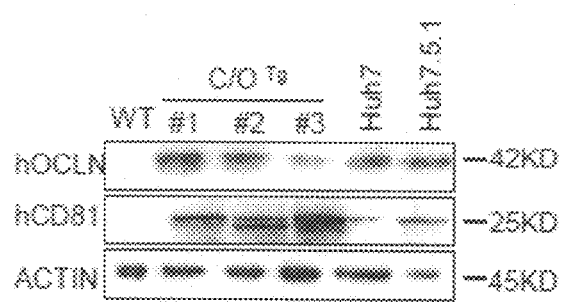
FIG. 1C illustrates the expressions of human CD81 and OCLN in liver of the double transgenic mice, with Huh7 and Huh7.5.1 hepatoma cells as control group.
Figure 1D:
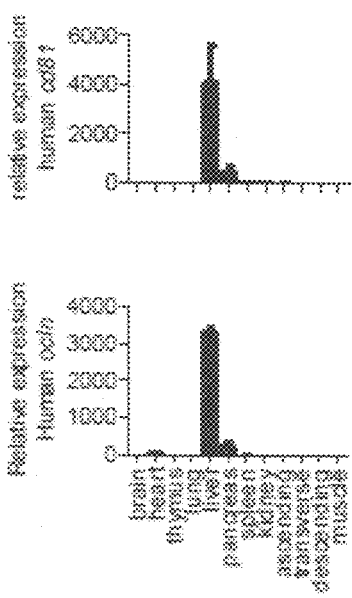
FIG. 1D illustrates the human CD81 and OCLN expressions in different tissues of the double transgenic mice by qRT-PCR.
Figure 1E:
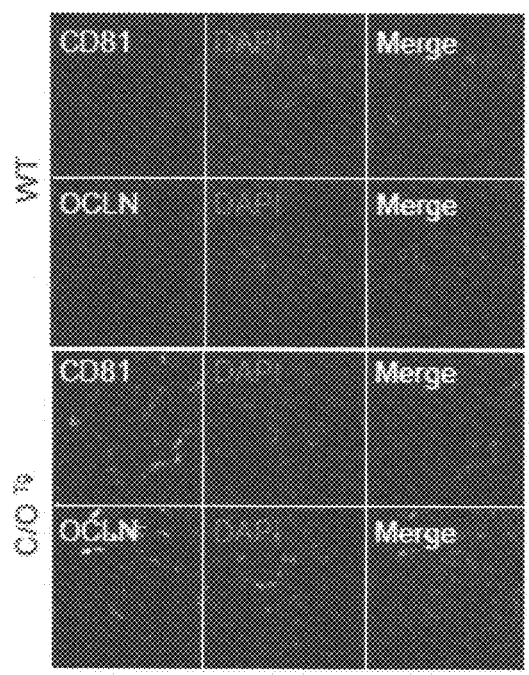
FIG. 1E illustrates the cellular localization of the human CD81 and OCLN in liver of the double transgenic mice.

Human CD81 and OCLN cDNA fragments obtained from human cDNA database were PCR amplified with the programmed conditions of the following: 95° C. for 10 minutes; 95° C. for 30 seconds; 58° C. for 30 seconds; 72° C. for 2 minutes; 33 cycles, and then 72° C. for 10 minutes to obtain human CD81 encoding DNA (cDNA) and OCLN encoding DNA (cDNA) respectively (Pfuultra II enzymes were purchased from Agliant company). CD81 cDNA was inserted into a pLIVE® vector in restriction sites between XhoI and BamHI endonuclease to obtain a pLIVE-CD81 vector containing CD81 expression. OCLN DNA (cDNA) was inserted into a pLIVE® vector in restriction sites between SalI and XhoI endonuclease to obtain a pLIVE-OCLN vector containing OCLN expression (endonucleases were purchased from NEB Inc.; pLIVE® vector was purchased from Minis Corporation). The pLIVE-CD81 vectors were excised by BglII and NdeI endonuclease to obtain a linear CD81 DNA fragment as shown in FIG. 1A (represented by SEQ ID NO. 3). The pLIVE-OCLN vector was excised by XbaI and NdeI endonuclease to obtain a linear OCLN DNA fragment as shown in FIG. 1A (representing SEQ ID NO. 4). Each DNA fragment was diluted to 1 ng/μL and microinjected into ICR mice zygotes respectively. The ICR mice zygotes were transplanted to pseudopregnant ICR mice uteruses to breed CD81 transgenic mice ($CD81^{Tg/-}$) and OCLN transgenic mice ($OCLN^{Tg/-}$) respectively. The CD81 transgenic mice and the OCLN transgenic mice were backcrossed to obtain the CD81 and OCLN double transgenic mice ($CD81^{Tg/-}$ $OCLN^{Tg/-}$, referring to as $C/O^{Tg}$). The genomic integration of the transgenes CD81 and OCLN in the double transgenic $C/O^{Tg}$ mice were verified and the results are shown in FIG. 1B. The expression of cognate receptor proteins in the double transgenic $C/O^{Tg}$ mice was verified and the results are shown in FIG. 1C. Furthermore, both human CD81 and OCLN had a dominant hepatic expression as shown in FIG. 1D with expected hepatic cell surface localization as shown in FIG. 1E.

Example 2

Construction of HCV Persistent Infection Model

Figure 2A:
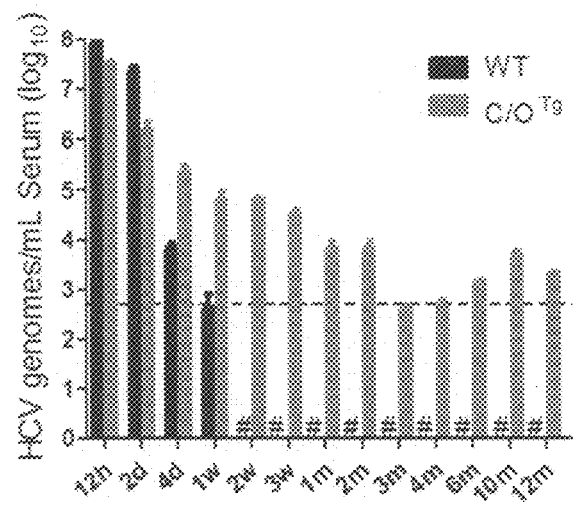
FIG. 2A illustrates the double transgenic mice and control group infected with HCV by tail vein injection respectively, and then the double transgenic mice ($C/O^{Tg}$, n=4) and control group (n=3) were sacrificed at indicated time for analyzing viral loads in serum.
Figure 2B:
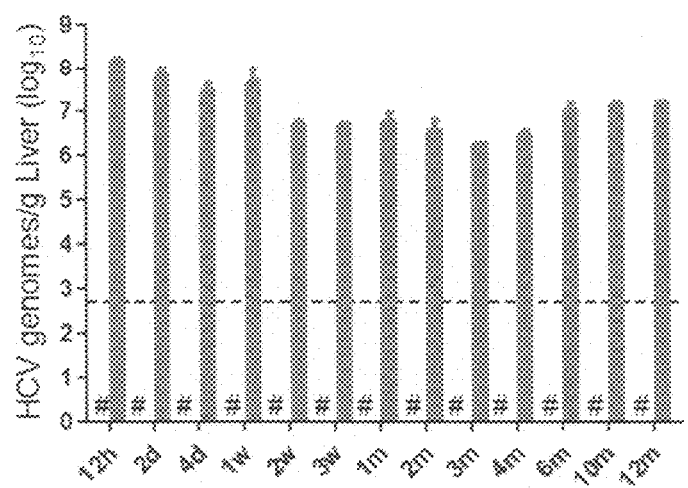
FIG. 2B illustrates the double transgenic mice and control group infected with HCV by tail vein injection respectively, and then the viral loads in liver of double transgenic mice ($C/O^{Tg}$, n=4) and control group (n=3) were sacrificed at indicated time for analyzing viral loads in serum.
Figure 2C:
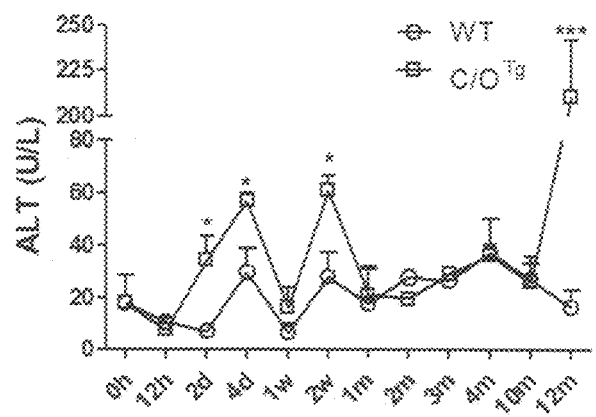
FIG. 2C illustrates the double transgenic mice and control group infected HCV by tail vein injection respectively, and then the double transgenic mice ($C/O^{Tg}$, n=4) and control group (n=3) were sacrificed at indicated time for analyzing alanine transaminase (ALT) level.
Figure 2D:
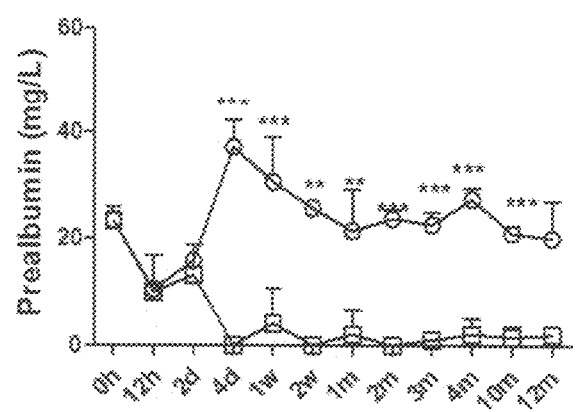
FIG. 2D illustrates the double transgenic mice and control group infected with HCV by tail vein injection respectively, and then the double transgenic mice ($C/O^{Tg}$, n=4) and control group (n=3) were sacrificed at indicated time for analyzing the prealbumin (PA) level in serum level
Figure 2E:
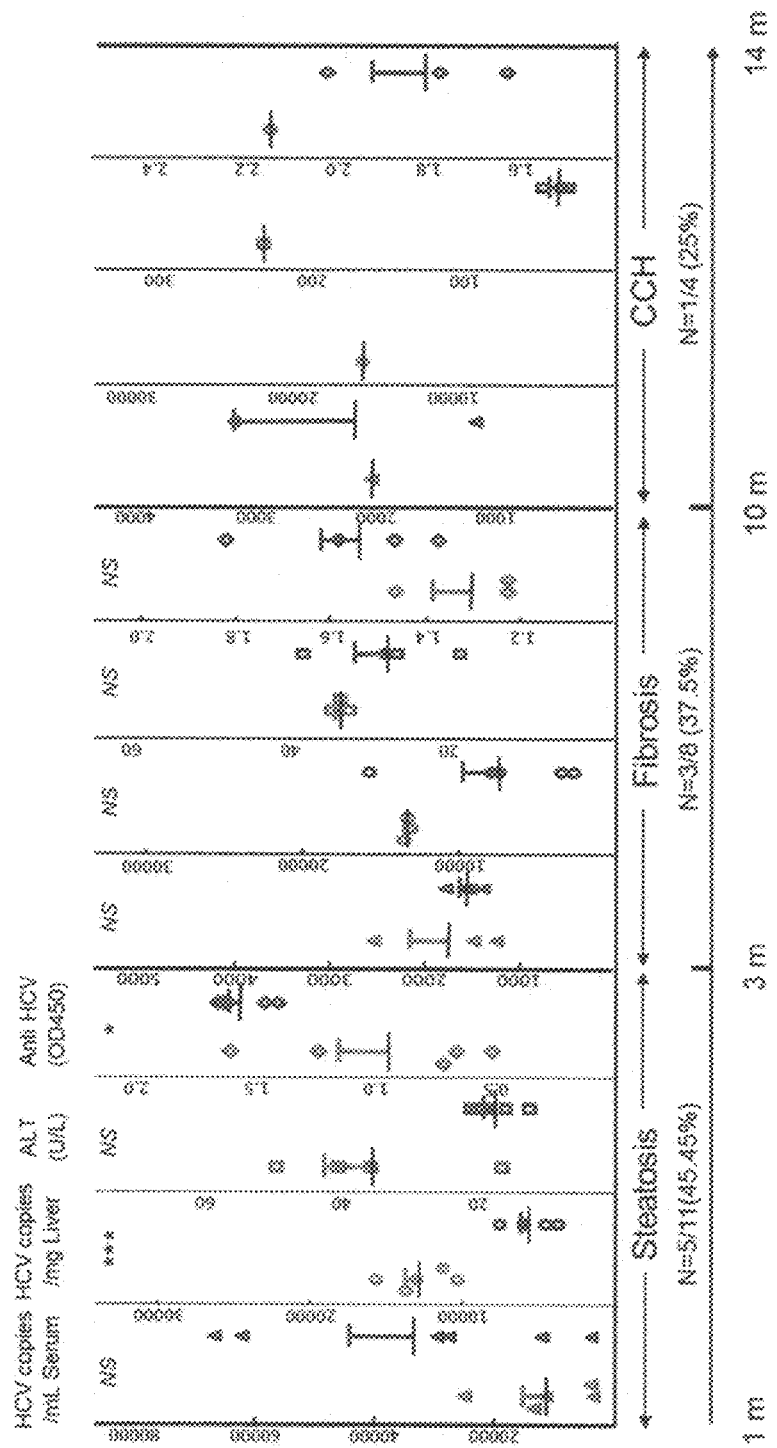
FIG. 2E illustrates the marker of the viral loads in serum and liver, liver injury (ALT level) and anti-HCV of the chronic infection cause steatosis (6 at 1 month post inoculation (mpi), 5 at 2 mpi, fibrotic (4 at 6 mpi, 4 at 10 mpi) and cirrhotic (4 at 13 mpi); wherein left dots indicate the double transgenic mice suffering pathological stage were verified as positive by ultrasonography, CT analysis and pathological evaluation.
Figure 3A:
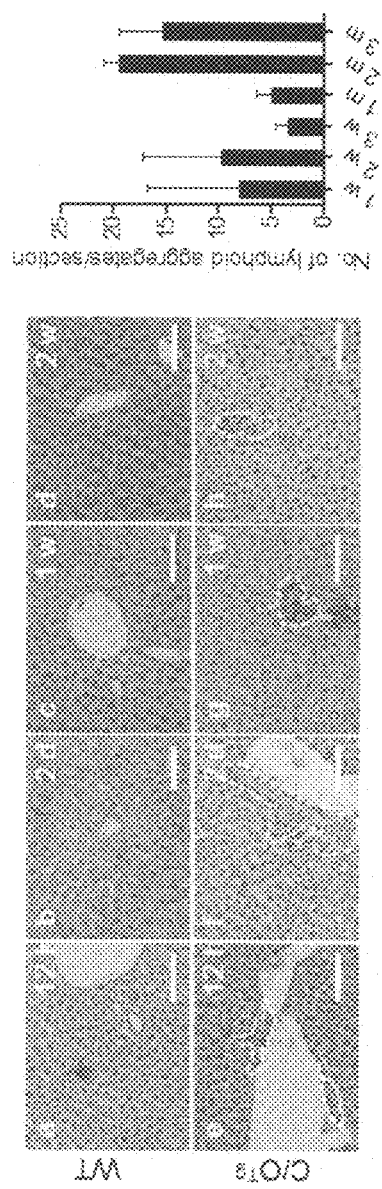
FIG. 3A illustrates the liver tissues of the double transgenic mice and control group by H&E stain (3 sections per mouse); wherein the broken lines in the FIG. 3A (e)-(f) respectively represent portal vein lymphoid infiltration; wherein the broken lines in the FIG. 3A (g)-(h) respectively represent lymphoid aggregate in hepatic lobule; the bar chart shows average number of lymphoid aggregated in each section.
Figure 3B:
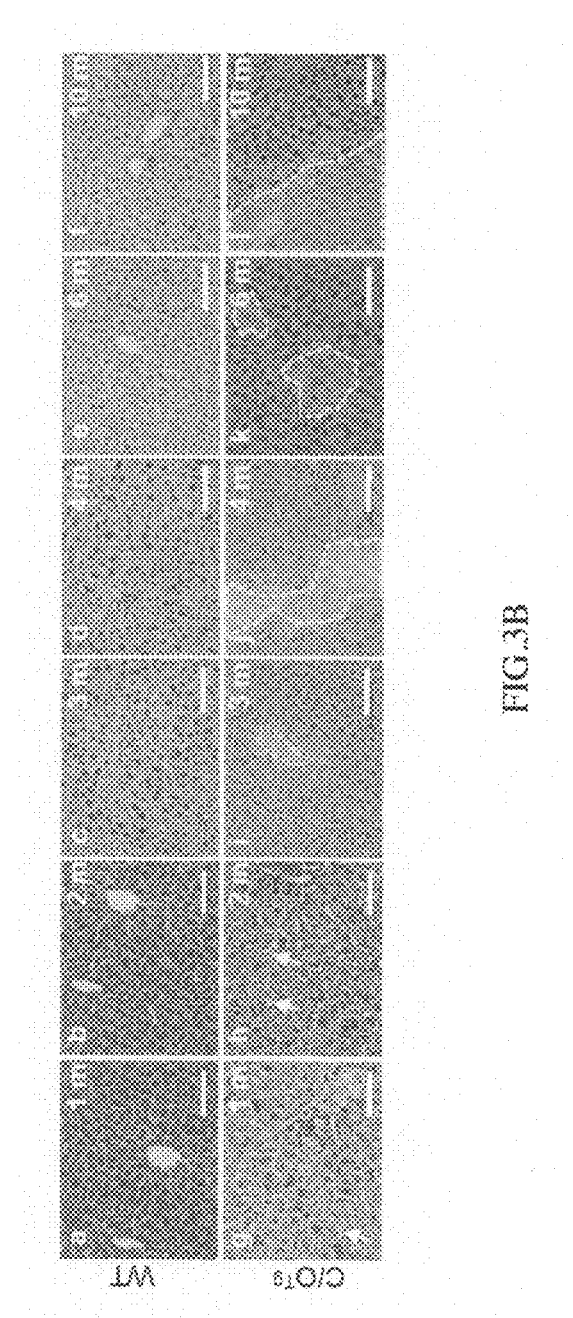
FIG. 3B illustrates micro vesicular steatosis (shown by the arrow), and amyloid depositions or tissue necrosis (shown by broken lines) of the double transgenic mice and control group by H&E stain.
Figures 3C, 3D:
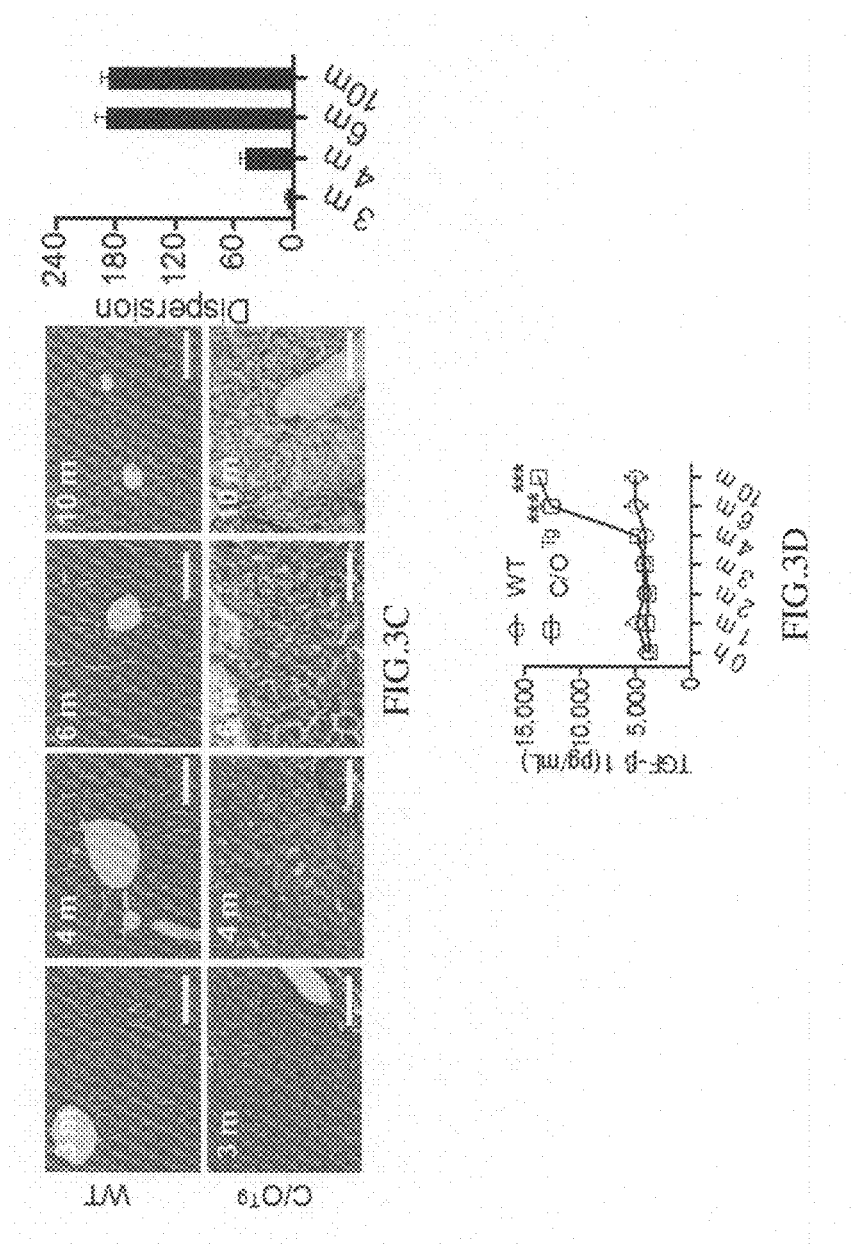
FIG. 3C illustrates fibrosis of liver sections of the double transgenic mice and control group by Masson's stain; wherein the level of fibrosis was quantified by dispersion degree (fibrosis area/fibrosis area quantity)
FIG. 3D illustrates the expression of transforming growth factor-β1 (TGF-β1) in serum after HCV infection of the double transgenic mice and control group.

Plasmid pJ399EM was transcribed in vitro (Han et al., 2009) to obtain a RNA, and then the RNA was electroporated into Huh7.5.1 cells (Pasteur Institute) for virus production during 96 hours and for collection, followed by ultrafiltration and purification to obtain HCV. The $C/O^{Tg}$ double transgenic mice or the wile type mice were injected at tail-vein with HCV ($TCID_{50}=1\times10^8$/mL) within 1-2 minutes. The serum or liver tissue of the $C/O^{Tg}$ double transgenic mice or the wile type mice were collected respectively at indicated time 0 hour to 12 months after infection. HCV RNA level in serum (genomes/mL) and liver (genomes/g) were measured by qRT-PCR. The program was performed as follows: 50° C. for 30 minutes, 95° C. for 10 minutes, followed by 50 cycles at 95° C. for 30 seconds, 58° C. for 30 seconds, and 72° C. for 30 seconds. Primers used for detection were as follows: sense (forward primer): ATCACTCCCCTGTGAGGAACT (represented by SEQ ID NO. 5); anti-sense (reverse primer): GCGGGTTGATC-CAAGAAAGG (represented by SEQ ID NO. 6). The viral load in serum (genomes/mL) of the wild type mice after injection was: 53746900±747977 (12 hours), 25791242±8626787 (2 days), 7026±2797 (4 days), 433±73 (1 week), and then the viral copies in peripheral blood of wild type mice was undetectable after one week. The viral load in peripheral blood (genomes/mL) of the $C/O^{Tg}$ double transgenic mice after injection was: 3598678±3016340 (12 hours), 1607875±1304933 (2 days), 228942±174178 (4 days), 64505±6821 (1 week), 67622±4612 (2 weeks), 33671±13347 (3 weeks), 6921±4272 (1 month), 6739±4783 (2 months), 403±95 (3 months), 534±125 (4 months), 1375±198 (6 months), 4781±2969 (10 months), 2067±277 (12 months). The results showed that HCV can be sustained in the peripheral blood of the $C/O^{Tg}$ double transgenic mice. The viral copies cannot be detectable in liver of the wile type mice after injection. The viral copies in the liver (genomes/g) of the $C/O^{Tg}$ double transgenic mice after injection was:

149676500±26422459.09 (12 hours), 68863260±26554660 (2 days), 30167166±14023164 (4 days), 48183923±49326087 (1 week), 5221675±782099 (2 weeks), 4723475±570250 (3 weeks), 5649760±3372903 (1 month), 3597135±2671267 (2 months), 1831199±34834 (3 months), 3055570±565440 (4 months), 10729851±3954535 (6 months), 14392085±1902774 (10 months), 15543000±124774 (12 months). The results showed that HCV can be sustained in the liver of the C/O$^{Tg}$ double transgenic mice. Meanwhile, the liver tissues were used for pathological analysis (H&E stain, Masson's stain), ultrasound, CT and other non-invasive imaging analysis to assess hepatitis, liver damage (fibrosis and cirrhosis) and other typical HCV pathology caused by HCV infection. The double transgenic mice infected by HCV express mild hepatitis symptoms (most ALT<40). The ALT level of the wild type mice was (U/L): 17.8±11.08 (uninfected), 10.5 0.51 (12 hours), 7.0±1.42 (2 days), 29.5±9.19 (4 days), 6.6±3.54 (1 weeks), 28.2±8.84 (2 weeks), 17.7±13.33 (1 month), 27.9±1.69 (2 months), 26.5±0.70 (3 months), 37.4±12.90 (4 months), 27.3±6.01 (10 months), 16.5±6.29 (12 months). The ALT level of the C/O$^{Tg}$ double transgenic mice was (U/L): 17.8±11.01 (uninfected), 7.8±6.72 (12 hours), 28.0±1.25 (2 days), 57.3±3.88 (4 days), 16.3±7.72 (1 week), 61.0±5.65 (2 week), 21.2±11.16 (1 month), 19.6±0.68 (2 months), 27.4±10.25 (3 months), 36.3±4.06 (4 months), 35.7±5.44 (6 months), 19.5±3.79 (10 months), 232.3±26.89 (12 months). The results showed that the wild type mice injected with virus showed almost no hepatitis symptoms (ALT<40), while the C/O$^{Tg}$ double transgenic mice infected with virus had no hepatitis symptoms in most of the time, but only expressed hepatitis symptoms in the late stage (ALT>40) (FIG. 2C). The prealbumin levels of the wild type mice after injection were maintained at normal levels (20~30 mg/L), but the prealbumin levels of the C/O$^{Tg}$ double transgenic mice cannot be detectable 4 days after infection. It was suggesting that some liver damages were caused by viral infection (FIG. 2D). The liver of the C/O$^{Tg}$ double transgenic mice infected by HCV expressed lymphocytes aggregation by H&E stain. Each section showed that 5 to 20 numbers lymphocytes aggregation occurred in 1 week to 5 months after infection (FIG. 3A), steatosis (vesicular structure) occurred in 1 month to 2 months after infection, amyloid deposition in peripheral vascular after infection for 3 months to 6 months, and necrosis occurred in 10 months after infection (FIG. 3B). Masson stain results showed apparently that the collagen fibers aggregation (blue) after infection for 6 months indicated liver fibrosis. The dispersion degree (fibrosis area/fibrosis area number) was 60 in 3 months after infection, and was 180 within 6 and 10 months after infection, indicating fibrosis was increasing. The increasing expression of TGF-β1 also confirmed increasing fibrosis (FIG. 3D). The significant differences occurred between pathological positive group and pathological negative group within viral copies in liver and HCV antibody level in serum in the steatosis stage by comparing steatosis, fibrosis and cirrhosis of mice and pathological negative mice at the same time; the remaining had no significant differences (FIG. 2G). The above-described conclusions indicated that the double transgenic mice can support HCV replication and produce pathological processes as the clinic.

Example 3

Pharmacodynamic Evaluation of Antiviral Drug in Mice by Acute HCV Infection

Figure 4A:
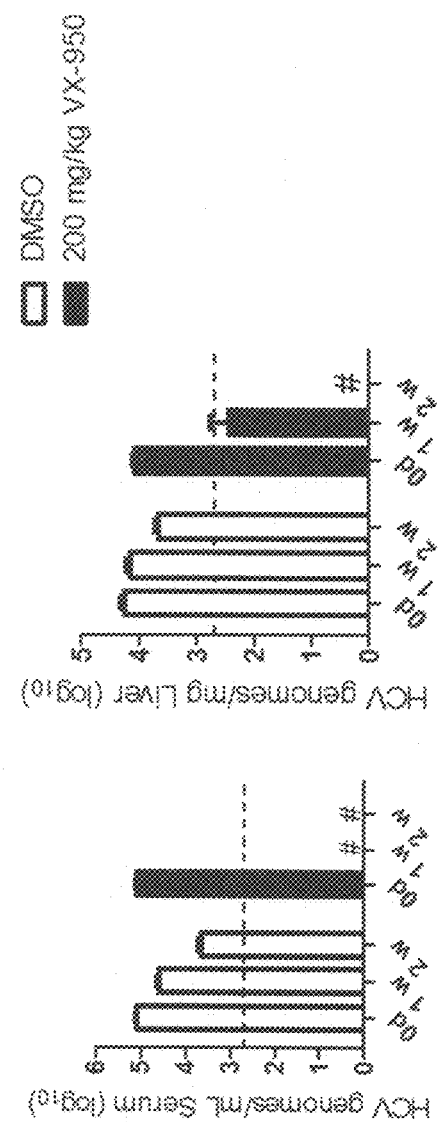
FIG. 4A illustrates HCV copies in serum and liver measured by qRT-PCR analysis, wherein the $C/O^{Tg}$ mice were injected with 200 mg/kg telaprevir drug after infected with HCV for 1 week; wherein the mice injected with DMSO served as a control group.
Figure 4B:
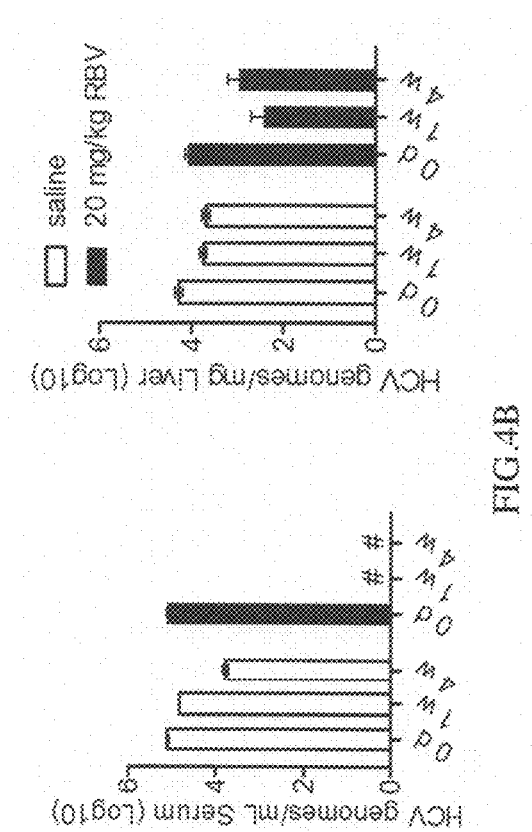
FIG. 4B illustrates HCV copies in serum and liver measured by qRT-PCR analysis while the $C/O^{Tg}$ mice were injected with 200 mg/kg Ribavirin drug after infected with HCV for 1 week; wherein the mice injected with DMSO served as a control group.
Figure 5:
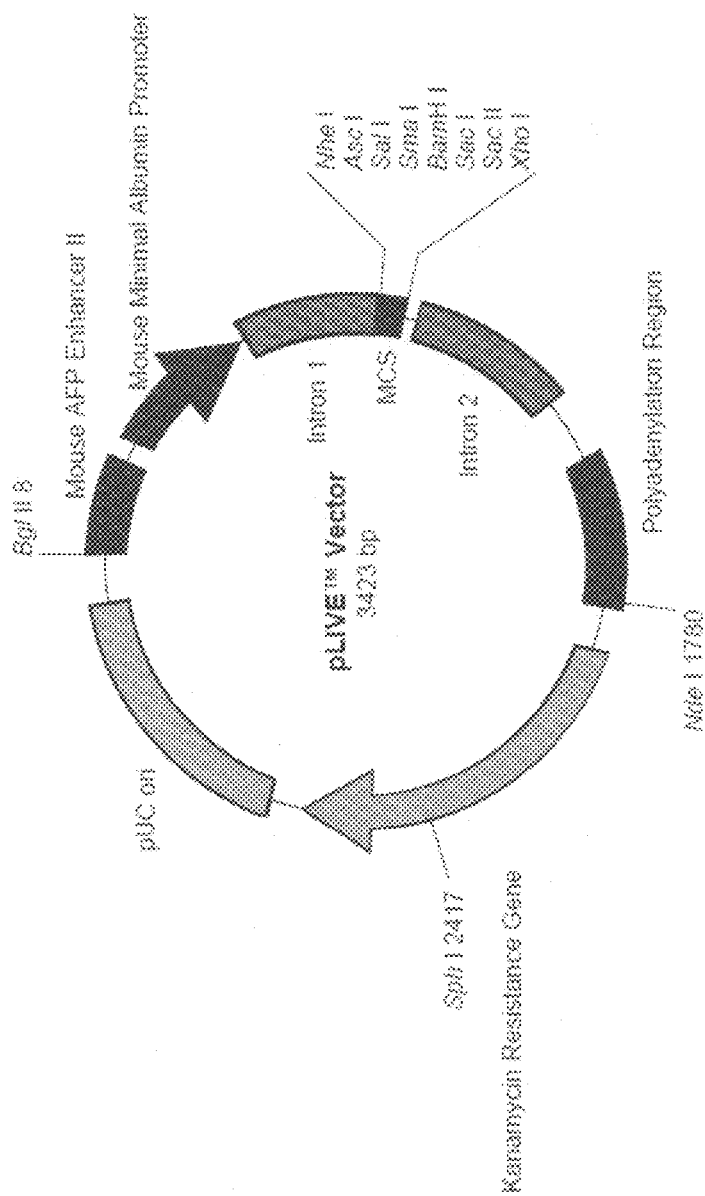
FIG. 5 illustrates a map of the pLIVE® vector.

The C/O$^{Tg}$ male mice were infected with HCV by tail vein injection (TCID$_{50}$=1×10$^8$) within 1-2 minutes. Starting medical treatment at a week after injection: 20 mg/kg Ribavirin (sigma) administered for 4 weeks by intraperitoneal injection daily or 200 mg/kg, Telaprevir (votex) administered for 2 weeks by intraperitoneal injection daily, wherein the antiviral drug was one component. The serum and liver tissues of the mice were collected after the treatment by Ribavirin for 1 week and 4 weeks, and by Telaprevir for 1 week and 2 weeks. HCV RNA copy numbers in the serum or liver cells were detected by qRT-PCR (Example 2). With respect to the untreated group, the viral copy number in the serum and liver was significantly decreasing after Ribavirin treatment, wherein the viral load in the peripheral blood (genomes/mL) of untreated group was: 123489±5761 (1 week after viral injection), 68312±214 (1 week after intraperitoneal injection of saline), 5958±1332 (1 month after intraperitoneal injection of saline); the viral load in the peripheral blood of treated group was 123489±5761 (1 week after viral injection), and the viral copies cannot be detected in peripheral blood by Ribavirin treatment for 1 week and 4 weeks. The viral copies in the liver (genomes/mg) in the untreated group was: 17864±3223 (1 week after viral injection), 5289±891 (1 week after saline intraperitoneal injection), 4713±916 (4 weeks after intraperitoneal injection of saline); treated group was: 17864±3223 (1 week after viral injection), 260±226 (1 week after Ribavirin injection), 894±639 (4 weeks after Ribavirin injection). The results showed that Ribavirin can effectively reduce the HCV copy number in serum and the HCV replication in the liver (FIG. 4A). Compared to untreated group, Telaprevir was a specific drug against HCV, significantly reduced the number of viral copies in serum and the replication in the after treatment, wherein the viral load in the peripheral blood (genomes/mL) in untreated group was: 123489±5761 (1 week after viral injection), 39782±5315 (1 week after DMSO intraperitoneal injection), 4349±1531 (1 month after DMSO intraperitoneal injection); while the treatment group was: 123489±5761 (1 week after viral injection), the viral copies in the peripheral blood cannot be detected after Telaprevir treatment for 1 week and 2 weeks. The viral copies in the liver (genomes/mg) in the untreated group was: 17864±3223 (1 week after viral injection), 14041±2712 (1 week after DMSO intraperitoneal injection), 4723±570 (4 weeks after DMSO intraperitoneal injection); treatment group was: 11836±1104 (1 week after viral injection), 273±301 (1 week after Telaprevir injection); the viral copies in the liver cannot be detected 4 weeks after Telaprevir treatment. The results showed that Ribavirin treatment can effectively reduce the number of HCV copies in serum and the HCV replication in the liver (FIG. 4B). The HCV infection model of double transgenic mice was sensitive to current drugs, and it suggested an excellent platform to assess HCV drugs.

What is claimed is:

1. A method to recapitulate human Hepatitis C virus (HCV) infection and replication comprising infecting a double transgenic ($C/O^{Tg}$) mouse whose genome comprises a human CD81 transgene and a human occludin (OCLN) transgene, the transgenes operably linked to a regulatory sequence for expressions of the human CD81 and OCLN in the liver of said mouse,
wherein the infection and replication of HCV in said mouse recapitulate human HCV life cycle to allow at least 50,000 genomes/mL HCV viral load in peripheral blood and at least 10,000,000 genomes/mL HCV viral load in the liver of said mouse for at least 4 days after HCV infection,
wherein the $C/O^{Tg}$ mouse is constructed by microinjecting a linear DNA fragment comprising a gene sequence encoding the human CD81 into a first Institute of Cancer Research (ICR) mouse zygote and microinjecting a linear DNA fragment comprising a gene sequence encoding the human OCLN into a second ICR mouse zygote;
transplanting the first ICR mouse zygote to a first pseudopregnant ICR mouse uterus to breed a CD81 transgenic mice and transplanting the second ICR mouse zygote to a second pseudopregnant ICR mouse uterus to breed a OCLN transgenic mice, and backcrossing the CD81 transgenic mice and the OCLN transgenic mice to generate the double transgenic $C/O^{Tg}$ mouse.

2. The method of claim 1, further comprising inserting the DC81 gene into a Liver in vivo Expression (pLIVE) vector to obtain a pLIVE-CD81 vector containing the CD81 gene and inserting the OCLN gene into a pLIVE vector to obtain a pLIVE-OCLN vector containing the OCLN gene, wherein the pLIVE vector comprises mouse α-fetoprotein (AFP) enhance and mouse albumin promoter to allow the transgenes to express in mouse liver.

3. The method of claim 1, further comprising confirming the generation of each of the CD81 transgenic mice and the OCLN transgenic mice by polymerase chain reaction (PCR) identification.

4. The method of claim 1, wherein the $C/O^{Tg}$ mouse is infected by injecting HCV directly into the $C/O^{Tg}$ mouse.

5. The method of claim 1, wherein the infected $C/O^{Tg}$ mouse has detectable viral copies in peripheral blood and/or liver after 6 months of infection.

6. The method of claim 1, wherein the infected $C/O^{Tg}$ mouse has detectable viral copies in peripheral blood and/or liver after 12 months of infection.

7. The method of claim 1, wherein the viral load in the infected $C/O^{Tg}$ mouse can be effectively reduced by antiviral drug(s).

8. The method of claim 7, wherein the antiviral drug is Ribavirin or Telaprevir.

9. The method of claim 1, wherein the CD81 and OCLN transgenes in the $C/O^{Tg}$ mouse do not replace the endogenous mouse CD81 and OCLN allelic genes.

* * * * *

SEQUENCE LISTING

<160> NUMBER OF SEQ ID NOS: 6

<210> SEQ ID NO 1
<211> LENGTH: 711
<212> TYPE: DNA
<213> ORGANISM: Homo sapiens

<400> SEQUENCE: 1

```
atgggagtgg agggctgcac caagtgcatc aagtacctgc tcttcgtctt caatttcgtc      60
ttctggctgg ctggaggcgt gatcctgggt gtggccctgt ggctccgcca tgacccgcag     120
accaccaacc tcctgtatct ggagctggga gacaagcccg cgcccaacac cttctatgta     180
ggcatctaca tcctcatcgc tgtgggcgct gtcatgatgt tcgttggctt cctgggctgc     240
tacggggcca tccaggaatc ccagtgcctg ctggggacgt tcttcacctg cctggtcatc     300
ctgtttgcct gtgaggtggc cgccggcatc tggggctttg tcaacaagga ccagatcgcc     360
aaggatgtga agcagttcta tgaccaggcc ctacagcagg ccgtggtgga tgatgacgcc     420
aacaacgcca aggctgtggt gaagaccttc acgagacgc ttgactgctg ggctccagc      480
acactgactg ctttgaccac ctcagtgctc aagaacaatt tgtgtccctc gggcagcaac     540
atcatcagca acctcttcaa ggaggactgc accagaaga tcgatgacct cttctccggg      600
aagctgtacc tcatcggcat tgctgccatc gtggtcgctg tgatcatgat cttcgagatg     660
atcctgagca tggtgctgtg ctgtggcatc cggaacagct ccgtgtactg a              711
```

<210> SEQ ID NO 2
<211> LENGTH: 1569
<212> TYPE: DNA
<213> ORGANISM: Homo sapiens

<400> SEQUENCE: 2

```
atgtcatcca ggcctcttga aagtccacct ccttacaggc ctgatgaatt caaaccgaat      60
cattatgcac caagcaatga catatatggt ggagagatgc atgttcgacc aatgctctct     120
cagccagcct actcttttta cccagaagat gaaattcttc acttctacaa atggaccttct    180
cctccaggag tgattcggat cctgtctatg ctcattattg tgatgtgcat tgccatcttt     240
gcctgtgtgg cctccacgct tgcctgggac agaggctatg gaacttccct tttaggaggt     300
agtgtaggct acccttatgg aggaagtggc tttggtagct acggaagtgg ctatggctat     360
ggctatggtt atggctatgg ctacggaggc tatacagacc caagagcagc aaagggcttc     420
atgttggcca tggctgcctt tgtttcatt gccgcgttgg tgatctttgt taccagtgtt     480
ataagatctg aaatgtccag aacaagaaga tactacttaa gtgtgataat agtgagtgct     540
atcctgggca tcatggtgtt tattgccaca attgtctata taatgggagt gaacccaact     600
gctcagtctt ctggatctct atatggttca caaatatatg ccctctgcaa ccaattttat     660
acacctgcag ctactggact ctacgtggat cagtatttgt atcactactg tgttgtggat     720
ccccaggagg ccattgccat tgtactgggg ttcatgatta ttgtggcttt tgctttaata     780
atttctttg ctgtgaaaac tcgaagaaag atggacaggt atgacaagtc caatatttg      840
tgggacaagg aacacatttta tgatgagcag cccccaatg tcgaggagtg ggttaaaaat     900
gtgtctgcag gcacacagga cgtgccttca ccccatctg actatgtgga aagagttgac     960
agtcccatgg catactcttc caatggcaaa gtgaatgaca agcggtttta tccagagtct    1020
tcctataaat ccacgccggt tcctgaagtg gttcaggagc ttccattaac ttcgcctgtg    1080
gatgacttca ggcagcctcg ttacagcagc ggtggtaact tgagacacc ttcaaaaaga    1140
gcacctgcaa agggaagagc aggaaggtca aagagaacag agcaagatca ctatgagaca    1200
gactacacaa ctggcggcga gtcctgtgat gagctggagg aggactggat cagggaatat    1260
ccacctatca cttcagatca acaaagacaa ctgtacaaga ggaatttga cactggccta    1320
```

-continued

| | |
|---|---|
| caggaataca agagcttaca atcagaactt gatgagatca ataaagaact ctcccgtttg | 1380 |
| gataaagaat tggatgacta tagagaagaa agtgaagagt acatggctgc tgctgatgaa | 1440 |
| tacaatagac tgaagcaagt gaagggatct gcagattaca aaagtaagaa gaatcattgc | 1500 |
| aagcagttaa agagcaaatt gtcacacatc aagaagatgg ttggagacta tgatagacag | 1560 |
| aaaacatag | 1569 |

<210> SEQ ID NO 3
<211> LENGTH: 2478
<212> TYPE: DNA
<213> ORGANISM: Artificial Sequence
<220> FEATURE:
<223> OTHER INFORMATION: CD81 DNA linear fragment excised from
      pLIVE-CD81 vector

<400> SEQUENCE: 3

| | |
|---|---|
| gatcttttg atggcagagt tcagtttacc gggtcacatt gtacctggga agattcaagg | 60 |
| atttatggaa aaagtcaaca acaggagtca gagcagccgg aaaagcatgg actctgtact | 120 |
| taggactgcg ctttgagcaa tggcacagca agctttaacc ctgtttgcag tcagcacaca | 180 |
| aactgtggtt caaagctcca ctttatctct tcttgtggaa ttcagatatc agatcagttt | 240 |
| aaaccttgcg gccgcactag tgctcaaatg ggagacaaag agattaagct cttatgtaaa | 300 |
| atttgctgtt ttcataaact ttaatgaatg gacaaagtct tgtgcatggg gtgggggtg | 360 |
| gggttagagg ggaacagctc cagatggcaa acatacgcaa gggatttagt caaacaactt | 420 |
| tttggcaaag atggtatgat tttgtaatgg ggtaggaacc aatgaaatgc gaggtaagta | 480 |
| tggttaataa tctacagtta ttggttaaag aagtatatta gagcgagtct ttctgcacac | 540 |
| agatcacctt cctatcaacc ccactagcct ctggcaaagg taccagtgta caggtttgtt | 600 |
| tcctttttta aaatacattg agtatgcttg ccttttagat atagaaatat ctgatgctgt | 660 |
| cttcttcact aaattttgat tacatgattt gacagcaata ttgaagagtc taacagccag | 720 |
| cacgcaggtt ggtaagtact gtgggaacat cacagatttt ggctccatgc cctaaagaga | 780 |
| aattggcttt cagattattt ggattaaaaa caaagacttt cttaagagat gtaaaatttt | 840 |
| catgatgttt tcttttttgc taaaactaaa gaattattct tttacatttc agttttctg | 900 |
| ctagcaggcg cgccagtcga ctcccgggat ccgccaccat gggagtggag ggctgcacca | 960 |
| agtgcatcaa gtacctgctc ttcgtcttca atttcgtctt ctggctggct ggaggcgtga | 1020 |
| tcctgggtgt ggccctgtgg ctccgccatg acccgcagac caccaacctc tgtatctgg | 1080 |
| agctgggaga caagcccgcg cccaacacct tctatgtagg catctacatc ctcatcgctg | 1140 |
| tgggcgctgt catgatgttc gttggcttcc tgggctgcta cggggccatc caggaatccc | 1200 |
| agtgcctgct ggggacgttc ttcacctgcc tggtcatcct gtttgcctgt gaggtggccg | 1260 |
| ccggcatctg ggctttgtc aacaaggacc agatcgccaa ggatgtgaag cagttctatg | 1320 |
| accaggccct acagcaggcc gtggtggatg atgacgccaa caacgccaag ctgtggtga | 1380 |
| agaccttcca cgagacgctt gactgctgtg gctccagcac actgactgct ttgaccacct | 1440 |
| cagtgctcaa gaacaatttg tgtccctcgg gcagcaacat catcagcaac ctcttcaagg | 1500 |
| aggactgcca ccgaagatc gatgacctct tctccgggaa gctgtacctc atcggcattg | 1560 |
| ctgccatcgt ggtcgctgtg atcatgatct tcgagatgat cctgagcatg gtgctgtgct | 1620 |
| gtggcatccg gaacagctcc gtgtactgac tcgagtaaca tcacatttaa aagcatctca | 1680 |
| ggtaactata ttttgaattt tttaaaaaag taactgtaat agttattatt aaaatagcaa | 1740 |

-continued

| | |
|---|---|
| agattgacca tttccaagag ccatatagac cagcaccgac cactattcta aactatttat | 1800 |
| gtatgtaaat attagctttt aaaattctca aaatagttgc tgagttggga accactatta | 1860 |
| tttctatcga ttcagcagcc gtaagtctag gacaggctta aattgttttc actggtgtaa | 1920 |
| attgcagaaa gatgatctaa gtaatttggc atttatttta ataggtttga aaaacacatg | 1980 |
| ccattttaca ataagactt atatttgtcc ttttgttttt cagcctacca tgagaataag | 2040 |
| agaaagaaaa tgaagatcaa aagcttattc atctgttttt cttttcgtt ggtgtaaagc | 2100 |
| caacaccctg tctaaaaaac ataaatttct ttaatcattt tgcctctttt ctctgtgctt | 2160 |
| caattaataa aaaatggaaa gaatctaata gagtggtaca gcactgttat ttttcaaaga | 2220 |
| tgtgttgcta tcctgaaaat tctgtaggtt ctgtggaagt tccagtgttc tctcttattc | 2280 |
| cacttcggta gaggatttct agtttcttgt gggctaatta aataaatcat taatactctt | 2340 |
| ctaagttatg gattataaac attcaaaata atattttgac attatgataa ttctgaataa | 2400 |
| aagaacaaaa accatggtat aggtaaggaa tataaaacat ggcttttacc ttagaaaaaa | 2460 |
| caattctaaa attcatat | 2478 |

<210> SEQ ID NO 4
<211> LENGTH: 4061
<212> TYPE: DNA
<213> ORGANISM: Artificial Sequence
<220> FEATURE:
<223> OTHER INFORMATION: OCLN DNA linear fragment excised from
      pLIVE-OCLN vector

<400> SEQUENCE: 4

| | |
|---|---|
| ctagagttcc actgagcgtc agaccccgta gaaaagatca aaggatcttc ttgagatcct | 60 |
| ttttttctgc gcgtaatctg ctgcttgcaa acaaaaaaac caccgctacc agcggtggtt | 120 |
| tgtttgccgg atcaagagct accaactctt tttccgaagg taactggctt cagcagagcg | 180 |
| cagataccaa atactgtcct tctagtgtag ccgtagttag gccaccactt caagaactct | 240 |
| gtagcaccgc ctacatacct cgctctgcta atcctgttac cagtggctgc tgccagtggc | 300 |
| gataagtcgt gtcttaccgg gttggactca agacgatagt taccggataa ggcgcagcgg | 360 |
| tcgggctgaa cggggggttc gtgcacacag cccagcttgg agcgaacgac ctacaccgaa | 420 |
| ctgagatacc tacagcgtga gctatgagaa agcgccacgc ttcccgaagg gagaaaggcg | 480 |
| gacaggtatc cggtaagcgg cagggtcgga acaggagagc gcacgaggga gcttccaggg | 540 |
| ggaaacgcct ggtatcttta tagtcctgtc gggtttcgcc acctctgact tgagcgtcga | 600 |
| tttttgtgat gctcgtcagg ggggcggagc ctatggaaaa acgccagcaa cgcggccttt | 660 |
| ttacggttcc tggccttttg ctggcctttt gctcacatgg ctcgacagat cgcggccgca | 720 |
| agagatcatt aattaagatc ttttgatgg cagagttcag tttaccgggt cacattgtac | 780 |
| ctgggaagat tcaaggattt atggaaaaag tcaacaacag gagtcagagc agccggaaaa | 840 |
| gcatggactc tgtacttagg actgcgcttt gagcaatggc acagcaagct taaccctgt | 900 |
| ttgcagtcag cacacaaact gtggttcaaa gctccacttt atctcttctt gtggaattca | 960 |
| gatatcagat cagtttaaac cttgcggccg cactagtgct caaatgggag acaaagagat | 1020 |
| taagctctta tgtaaaattt gctgttttac ataactttaa tgaatggaca agtcttgtg | 1080 |
| catgggggtg ggggtggggt tagaggggaa cagctccaga tggcaaacat acgcaaggga | 1140 |
| tttagtcaaa caacttttg gcaaagatgg tatgattttg taatgggta ggaaccaatg | 1200 |
| aaatgcgagg taagtatggt taataatcta cagttattgg ttaaagaagt atattagagc | 1260 |

```
gagtctttct gcacacagat caccttccta tcaaccccac tagcctctgg caaaggtacc    1320
agtgtacagg tttgtttcct ttttaaaat acattgagta tgcttgcctt ttagatatag     1380
aaatatctga tgctgtcttc ttcactaaat tttgattaca tgatttgaca gcaatattga    1440
agagtctaac agccagcacg caggttggta agtactgtgg aacatcaca gattttggct     1500 ccatgcccta aagagaaatt ggctttcaga ttatttggat taaaaacaaa gactttctta    1560
agagatgtaa aattttcatg atgttttctt ttttgctaaa actaaagaat tattctttta    1620
catttcagtt tttctgctag caggcgcgcc agtcgacgcc accatgtcat ccaggcctct    1680
tgaaagtcca cctccttaca ggcctgatga attcaaaccg aatcattatg caccaagcaa    1740
tgacatatat ggtggagaga tgcatgttcg accaatgctc tctcagccag cctactcttt    1800
ttacccagaa gatgaaattc ttcacttcta caaatggacc tctcctccag gagtgattcg    1860
gatcctgtct atgctcatta ttgtgatgtg cattgccatc tttgcctgtg tggcctccac    1920
gcttgcctgg gacagaggct atggaacttc cctttagga ggtagtgtag ctacccctta    1980
tggaggaagt ggctttggta gctacggaag tggctatggc tatggctatg gttatggcta    2040
tggctacgga ggctatacag acccaagagc agcaaagggc ttcatgttgg ccatggctgc    2100
cttttgtttc attgccgcgt tggtgatctt tgttaccagt gttataagat ctgaaatgtc    2160
cagaacaaga agatactact taagtgtgat aatagtgagt gctatcctgg gcatcatggt    2220
gtttattgcc acaattgtct atataatggg agtgaaccca actgctcagt cttctggatc    2280
tctatatggt tcacaaatat atgccctctg caaccaattt tatacacctg cagctactgg    2340
actctacgtg gatcagtatt tgtatcacta ctgtgttgtg gatccccagg aggccattgc    2400
cattgtactg gggttcatga ttattgtggc ttttgcttta ataatttct ttgctgtgaa     2460 aactcgaaga aagatggaca ggtatgacaa gtccaatatt ttgtgggaca aggaacacat    2520
ttatgatgag cagcccccca atgtcgagga gtgggttaaa aatgtgtctg caggcacaca    2580
ggacgtgcct tcacccccat ctgactatgt ggaaagagtt gacagtccca tggcatactc    2640
ttccaatggc aaagtgaatg acaagcggtt ttatccagag tcttcctata aatccacgcc    2700
ggttcctgaa gtggttcagg agcttccatt aacttcgcct gtggatgact caggcagcc    2760 tcgttacagc agcggtggta actttgagac accttcaaaa agagcacctg caagggaag    2820 agcaggaagg tcaaagagaa cagagcaaga tcactatgag acagactaca aactggcgg    2880 cgagtcctgt gatgagctgg aggaggactg gatcagggaa tatccaccta tcacttcaga    2940
tcaacaaaga caactgtaca agaggaattt tgacactggc ctacaggaat acaagagctt    3000
acaatcagaa cttgatgaga tcaataaaga actctcccgt ttggataaag aattggatga    3060
ctatagagaa gaaagtgaag agtacatggc tgctgctgat gaatacaata gactgaagca    3120
agtgaaggga tctgcagatt acaaaagtaa gaagaatcat tgcaagcagt taaagagcaa    3180
attgtcacac atcaagaaga tggttggaga ctatgataga cagaaacat agctcgagta    3240 acatcacatt taaaagcatc tcaggtaact atattttgaa tttttaaaa aagtaactgt    3300 aatagttatt attaaaatag caaagattga ccatttccaa gagccatata gaccagcacc    3360
gaccactatt ctaaactatt tatgtatgta aatattagct tttaaaattc tcaaaatagt    3420
tgctgagttg ggaaccacta ttatttctat cgattcagca gccgtaagtc taggacaggc    3480
ttaaattgtt ttcactggtg taaattgcag aaagatgatc taagtaattt ggcatttatt    3540
ttaataggtt tgaaaacac atgccatttt acaataaga cttatatttg tccttttgtt     3600
tttcagccta ccatgagaat aagagaaaga aaatgaagat caaaagctta tcatctgtt    3660
```

-continued

```
tttcttttc  gttggtgtaa  agccaacacc  ctgtctaaaa  aacataaatt  tctttaatca    3720
ttttgcctct  tttctctgtg  cttcaattaa  taaaaaatgg  aaagaatcta  atagagtggt    3780
acagcactgt  tattttcaa   agatgtgttg  ctatcctgaa  aattctgtag  gttctgtgga    3840
agttccagtg  ttctctctta  ttccacttcg  gtagaggatt  tctagtttct  tgtgggctaa    3900
ttaaataaat  cattaatact  cttctaagtt  atggattata  aacattcaaa  ataatatttt    3960
gacattatga  taattctgaa  taaaagaaca  aaaaccatgg  tataggtaag  gaatataaaa    4020
catggctttt  accttagaaa  aaacaattct  aaaattcata  t                        4061

<210> SEQ ID NO 5
<211> LENGTH: 21
<212> TYPE: DNA
<213> ORGANISM: Artificial Sequence
<220> FEATURE:
<223> OTHER INFORMATION: FORWARD PRIMER

<400> SEQUENCE: 5
atcactcccc tgtgaggaac t                                                    21

<210> SEQ ID NO 6
<211> LENGTH: 20
<212> TYPE: DNA
<213> ORGANISM: Artificial Sequence
<220> FEATURE:
<223> OTHER INFORMATION: REVERSE PRIMER

<400> SEQUENCE: 6
gcgggttgat ccaagaaagg                                                      20
```